United States Patent
Adibhatla et al.

(10) Patent No.: US 9,750,700 B2
(45) Date of Patent: Sep. 5, 2017

(54) IMATINIB MESYLATE ORAL PHARMACEUTICAL COMPOSITION AND PROCESS FOR PREPARATION THEREOF

(75) Inventors: Kali Satya Bhujanga Rao Adibhatla, Hyderabad (IN); Venkaiah Chowdary Nannapaneni, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 0 days.

(21) Appl. No.: 13/166,499

(22) Filed: Jun. 22, 2011

(65) Prior Publication Data
US 2012/0329810 A1 Dec. 27, 2012

(51) Int. Cl.
| *A61K 31/44* | (2006.01) |
| *A61K 31/444* | (2006.01) |
| *C07D 213/06* | (2006.01) |
| *C07D 221/16* | (2006.01) |
| *A61K 9/20* | (2006.01) |
| *A61K 9/16* | (2006.01) |

(52) U.S. Cl.
CPC .......... *A61K 9/2013* (2013.01); *A61K 9/1688* (2013.01)

(58) Field of Classification Search
IPC ....... A61K 31/44,31/444, 9/2013, 9/617; C07D 213/06, 221/16
See application file for complete search history.

(56) References Cited

U.S. PATENT DOCUMENTS

| 6,894,051 B1 | 5/2005 | Zimmermann et al. | |
| 9,238,571 B2 * | 1/2016 | Ward | A61K 9/1617 |
| 2005/0267125 A1 * | 12/2005 | Luftensteiner et al. | 514/252.18 |
| 2006/0092669 A1 * | 5/2006 | Chen | 362/619 |
| 2006/0275372 A1 * | 12/2006 | Jenkins et al. | 424/489 |
| 2010/0203133 A1 | 8/2010 | Luftensteiner et al. | |
| 2011/0206827 A1 | 8/2011 | Röhrich et al. | |

FOREIGN PATENT DOCUMENTS

| EP | 0564409 A1 | 10/1993 |
| EP | 1888040 | * 11/2006 |
| EP | 1 762 230 | 3/2007 |
| EP | 1501485 B1 | 9/2007 |
| EP | 2497464 | * 9/2012 |
| WO | 99/03854 A1 | 1/1999 |
| WO | WO 2005/020978 | * 3/2005 |
| WO | WO 2006/040779 | * 4/2006 |
| WO | WO 2009/135949 | 11/2009 |
| WO | WO 2011/121593 | 10/2011 |
| WO | WO 2011/160798 | 12/2011 |
| WO | WO 2012/019633 | * 2/2012 |

OTHER PUBLICATIONS

International Search Report for International Application No. PCT/IB2011/001803 mailed Mar. 26, 2012.
Third Party Submission submitted in corresponding EP Application No. 11763979.9 on Sep. 16, 2015; 4 pages.

* cited by examiner

*Primary Examiner* — Shirley V Gembeh

(74) *Attorney, Agent, or Firm* — Mintz, Levin, Cohn, Ferris, Glovsky and Popeo, P.C.

(57) ABSTRACT

The invention relates to an oral pharmaceutical composition comprising, greater than 80% of Imatinib, by weight based on the total weight of the composition and the process for preparation thereof.

5 Claims, No Drawings

IMATINIB MESYLATE ORAL PHARMACEUTICAL COMPOSITION AND PROCESS FOR PREPARATION THEREOF

FIELD OF THE INVENTION

The present invention relates to an oral pharmaceutical composition, such as a tablet, including greater than 80% of Imatinib by weight based on the total weight of the composition and the process for preparation thereof.

BACKGROUND OF THE INVENTION

Imatinib mesylate is chemically designated as 4-(4-methylpiperazin-1-ylmethyl)-N-[4-methyl-3-(4-pyridin-3-yl) pyrimidin-2-ylamino) phenyl]-benzamide methane sulfonate and its structural formula is

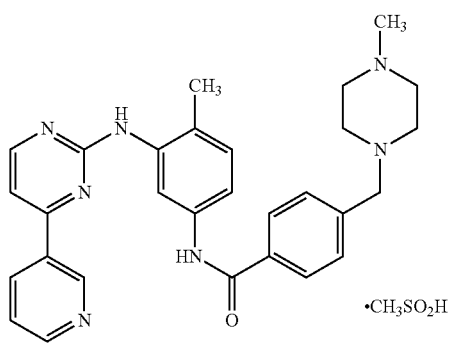

Imatinib is a protein-tyrosine kinase inhibitor, especially useful in the treatment of various types of cancer and can also be used for the treatment of atherosclerosis, thrombosis, restenosis, or fibrosis. Thus Imatinib is used for the treatment of non-malignant diseases. Imatinib is usually administered orally in the form of suitable salt, e.g., in the form of Imatinib mesylate.

Imatinib mesylate is a white to off white to brownish or yellow tinged crystalline powder. Imatinib mesylate is soluble in aqueous buffers ≤pH 5.5 but is very slightly soluble to in soluble in neutral/alkaline aqueous buffers. In non-aqueous solvents, the drug substance is freely soluble to very slightly soluble in dimethyl sulfoxide, methanol and ethanol, but is insoluble in n-octanol, acetone and acetonitrile.

Imatinib mesylate is sold under the brand name Gleevac® which is marketed by Novartis Pharmaceuticals. Gleevac® is available in tablets for oral administration in 100 and 400 mg strength. The inactive ingredients of Gleevac® are colloidal silicon dioxide (NF); crospovidone (NF); hydroxy propyl methyl cellulose (USP); magnesium stearate (NF); and microcrystalline cellulose (NF). Tablet coating: ferric oxide, red (NF); ferric oxide, yellow (NF); hydroxy propyl methyl cellulose (USP); polyethylene glycol (NF); and talc (USP).

U.S. Pat. No. 6,894,051 describes the process for the preparation of the α- and β-crystalline form of Imatinib mesylate, the α-crystalline form being hygroscopic.

US Patent Application no. 20100203133A1, relates to the formulation of Imatinib containing 30-80% w/w of Imatinib. The tablet described in US Patent Application no. 20100203133A1 is convenient to administer and provides a daily dose amount of Imatinib. However, there exists a need to develop a pharmaceutical composition which is more convenient and easier to swallow to provide a daily dose of Imatinib.

SUMMARY OF THE INVENTION

In an embodiment the present invention provides an oral pharmaceutical composition, which can be in the form of a tablet, including greater than 80% of Imatinib, by weight based on the total weight of the composition.

In another embodiment the present invention provides the processes for preparing an oral pharmaceutical composition, preferably a tablet, including greater than 80% of Imatinib by weight based on the total weight of the composition by a process of wet granulation.

DETAILED DESCRIPTION OF THE INVENTION

The present invention is defined in the claims. The present invention relates to an oral pharmaceutical composition, including greater than 80% of Imatinib by weight based on the total weight of the composition.

In an embodiment the present invention relates to an oral pharmaceutical composition, e.g., a tablet, including greater than 80% of Imatinib, by weight based on the total weight of the composition, a lubricant, and/or film coating.

In an embodiment of the present invention, Imatinib can be in the form of a salt, such as Imatinib Mesylate. In an embodiment, the Mesylate salt form of Imatinib can be in a crystalline form, e.g., alpha or beta crystal form.

Any of a variety of lubricants can be used in the present composition. Suitable lubricants include magnesium stearate, calcium stearate, aluminium stearate, sodium stearyl fumarate, talc, or a mixture thereof. The lubricant can be present in the intragranular portion, the extragranular portion, or in both the intra and extra granular portions.

The amount of the lubricant can be about 0.1% to about 5% w/w, e.g., about 1 to about 4% w/w, of the total composition.

The amount of the film coating can be about 1 to about 10% w/w, for example, about 1 to about 3% w/w, of the total composition. Any of a variety of film coatings can be used in the present composition. Suitable film coating materials for coating the core tablets of Imatinib include InstaCoat film coating material supplied by Ideal Cures Pvt. Ltd. Such a coating can include polymers, plasticizers, pigments, opacifiers, glidants, binders, antitacking agents, antifoaming agents, surfactants, fillers, extenders, and the like. Suitable polymers for the film coating system include hydroxypropylmethyl cellulose, polyvinyl alcohol, sodium alginate, cellulose acetate phthalate, hydroxy propyl methyl cellulose phthalate, methacrylic acid co-polymers, and the like. The coating can be obtained as a dry blend concentrate.

The present invention further relates to the process processes for preparing a pharmaceutical composition, for example, a tablet, including greater than 80% of Imatinib by weight based on the total weight of the composition by a process of wet granulation.

The present invention relates to a process of wet granulation of an Imatinib pharmaceutical composition, for example, a tablet by:

1) Dissolving/Dispersing a first portion of a lubricant in a solvent to form a lubricant solution/suspension;

2) Granulating Imatinib with the lubricant solution/suspension obtained in step 1 to form granules;

3) Lubricating the granules prepared in step 2 with a second portion of the lubricant to form a final blend;

4) Compressing the final blend obtained in step 3 to form a core tablet; and

5) Coating the core tablet(s) obtained in step 4 with a film coating suspension to form film coated tablets of Imatinib.

An embodiment of the present invention relates to a process of wet granulation of an Imatinib pharmaceutical composition, e.g., a tablet by:

1) Dissolving/Dispersing a lubricant in a solvent to form a lubricant solution/suspension;

2) Granulating Imatinib with the lubricant solution/suspension obtained in step 1 to form granules;

3) Compressing the granules obtained in step 2 to form a core tablet; and

4) Coating the core tablet(s) obtained in step 3 with a film coating suspension to form film coated tablets of Imatinib.

An embodiment of the present invention relates to a process of wet granulation of an Imatinib pharmaceutical composition, e.g., a tablet by:

1) Granulating Imatinib with a solvent to form the granules;

2) Lubricating the granules obtained in step 1 with a lubricant to form a lubricated blend;

3) Compressing the lubricated blend obtained in step 2 to form a core tablet;

4) Coating the core tablet(s) obtained in step 3 with a film coating suspension to form film coated tablets of Imatinib.

Any of a variety solvents can be used for forming the lubricated solution used in the present method. Suitable solvents include purified water, methanol, ethanol, isopropyl alcohol, dimethyl sulfoxide, or mixtures thereof. In an embodiment, purified water is used as a solvent for the lubricated solution.

An aspect of the present invention provides the process of wet granulation of an Imatinib pharmaceutical composition, e.g., a tablet by:

1. Dissolving/Dispersing a first portion of a lubricant in purified water to form a lubricant solution/suspension.
2. Granulating Imatinib (e.g., Imatinib mesylate) with the lubricant solution/suspension obtained in step 1 in a mixer (e.g., a high shear mixer) to form wet granules.
3. Drying the wet granules (e.g., in a fluid bed dryer) and passing them through a granulator (e.g., an oscillating granulator).
4. Lubricating the dry granules obtained in step 3 with a second portion of the lubricant in a blender, e.g., an Octagonal blender or a double cone blender.
5. Tabletting the mixture in the step 4 by compression, e.g., using a rotary tablet machine, to form core tablets.
6. Coating the core tablets with a film coating suspension in a coating pan, e.g., Neocota (Automatic coating machine).

An aspect of the present invention provides a process of wet granulation of an Imatinib pharmaceutical composition, e.g., a tablet by:

1. Dissolving/Dispersing a lubricant in a solvent (e.g., purified water) to form a lubricant solution or suspension.
2. Granulating Imatinib (e.g., Imatinib mesylate) with the lubricant solution/suspension obtained in step 1 in a mixer (e.g., a high shear mixer) to form wet granules.
3. Drying the wet granules (e.g., in a fluid bed dryer) and passing through a granulator (e.g., an oscillating granulator).
4. Tabletting the dry granules obtained in step 3 by compression, e.g., using a rotary tablet machine, to form core tablets.
5. Coating the core tablets with a film coating suspension in a coating pan, e.g., Neocota (Automatic coating machine).

An aspect of the present invention provides a process of wet granulation of an Imatinib pharmaceutical composition, e.g., a tablet by:

1. Granulating Imatinib (e.g. Imatinib mesylate) with a solvent (e.g., purified water) in a mixer (e.g., a high shear mixer) to form wet granules.
2. Drying the wet granules (e.g., in a fluid bed dryer) and passing them through a granulator (e.g., an oscillating granulator).
3. Lubricating the dry granules obtained in step 2 with a lubricant in a blender, e.g., an octagonal blender or a double cone blender, to form the lubricated blend.
4. Tabletting the lubricated blend obtained in step 3 by compression, e.g., using a rotary tablet machine, to form core tablets.
5. Coating the core tablets with the film coating suspension in the coating pan, e.g., Neocota (Automatic coating machine).

In an embodiment, the tablet obtained by the compression method described above can be round or oval. The edges of the tablets can be beveled or rounded. In an embodiment, the tablets are ovoid or round. The tablets according to the invention may be scored.

The ovoid tablet may be small in dimension, e.g., 10 to 20 mm in length, 15 to 20 mm in length, or 16 to 18 mm in length; 4 to 10 mm in width, 6 to 9 mm in width, or 7 to 8 mm in width. The thickness of the tablet can be from 4 to 8 mm, for example 5 to 8 mm or 6 to 7 mm. Compression forces of between 8 to 20 kg/cm$^2$ can be used to prepare the compressed tablet, for example, 10 to 18 kg/cm$^2$ or 10 to 16 kg/cm$^2$. In an embodiment, the ovoid tablet contains 400 mg of Imatinib. The invention also includes embodiments in which these dimensions of the ovoid tablet are modified by "about".

The round tablet may be of any suitable dimension, e.g., 5 to 15 mm in diameter, 6 to 10 mm in diameter, about 7 to 9 mm in diameter. In an embodiment, the thickness of the tablet can be from 1 to 5 mm; for example 2 to 5 mm or 3 to 5 mm. Compression forces of between 4 to 18 kg/cm$^2$ can be used to prepare the round compressed tablet, for example, 5 to 12 kg/cm$^2$ or 6 to 10 kg/cm$^2$. In an embodiment, the round tablet contains 100 mg of Imatinib. In an embodiment, the 100 mg tablet is a scored tablet. A scored tablet can have a break score on one side. The invention also includes embodiments in which these dimensions of the round tablet are modified by "about".

In an embodiment, the disintegrating time of the tablet can be about 20 minutes or less. In an embodiment, for a 100 mg Imatinib tablet, the disintegrating time is about 2 to 10 minutes, for example, 4 to 10 minutes. In an embodiment, for a 400 mg Imatinib tablet, the disintegration time is, for example, about 7 to 15 minutes or about 8 to 15 minutes.

The present invention may be better understood with reference to the following examples. These examples are intended to be representative of specific embodiments of the invention, and are not intended as limiting the scope of the invention.

EXAMPLE-1

TABLE 1

A composition of the present invention including 400 mg of Imatinib.

| S. No. | Ingredients | mg/Tab |
|---|---|---|
| | Intragranular portion | |
| 1 | Imatinib Mesylate | 478 |
| 2 | Sodium Stearyl Fumarate | 1 |
| 3 | Purified Water | q.s. |
| | Extragranular portion | |
| 4 | Sodium Stearyl Fumarate | 2 |
| | Film coating | |
| 5 | InstaCoat | 9 |
| 6 | Purified water | q.s. |
| | Total weight of the tablet | 490 |

Procedure:
1. The first portion of the sodium stearyl fumarate (present in the intragranular portion) was dissolved in the purified water to form the lubricated solution.
2. Imatinib mesylate was granulated with the lubricated solution obtained in step 1 in the rapid mixer granules to form the wet granules.
3. The wet granules were dried in the fluid bed dryer and passed through oscillating granulator.
4. The dry granules were lubricated with the second portion of the sodium stearyl fumarate (present in the extragranular portion) to form the lubricated blend.
5. The lubricated blend was compressed with the tabletting machine to form the core tablets.
6. The core tablets were coated with the film coating suspension (InstaCoat suspension) and formed the film coated tablets in a coating pan, e.g., Neocota (Automatic coating machine).

EXAMPLE-2

TABLE 2

A composition of the present invention including 100 mg of Imatinib.

| S. No. | Ingredients | mg/Tab |
|---|---|---|
| | Intragranular portion | |
| 1 | Imatinib Mesylate | 119.5 |
| 2 | Sodium Stearyl Fumarate | 0.5 |
| 3 | Purified Water | q.s. |
| | Extragranular portion | |
| 4 | Sodium Stearyl Fumarate | 0.5 |
| | Film coating | |
| 5 | InstaCoat | 2.5 |
| 6 | Purified water | q.s. |
| | Total weight of the tablet | 123 |

Procedure:
1. The first portion of the sodium stearyl fumarate (present in the intragranular portion) was dissolved in the purified water to form the lubricant solution.
2. Imatinib mesylate was granulated with the lubricant solution obtained in step 1 in the rapid mixer granules to form the wet granules.
3. The wet granules were dried in the fluid bed dryer and passed through oscillating granulator.
4. The dry granules were lubricated with the second portion of the sodium stearyl fumarate (present in the extragranular portion) to form the lubricated blend.
5. The lubricated blend was compressed with the tabletting machine to form the core tablets.
6. The core tablets were coated with the film coating suspension (InstaCoat suspension) and formed the film coated tablets in a coating pan, e.g., Neocota (Automatic coating machine).

EXAMPLE-3

TABLE 3

A composition of the present invention including 400 mg of Imatinib.

| S. No. | Ingredients | mg/Tab |
|---|---|---|
| | Tablet core | |
| 1 | Imatinib Mesylate | 478 |
| 2 | Magnesium Stearate | 3 |
| 3 | Purified Water | q.s. |
| | Film coating | |
| 4 | InstaCoat | 9 |
| 5 | Purified water | q.s. |
| | Total weight of the tablet | 490 |

Procedure:
1. Magnesium Stearate was dispersed in the purified water to form the lubricant suspension.
2. Imatinib mesylate was granulated with the lubricant suspension obtained in step 1 in the rapid mixer granulator to form the wet granules.
3. The wet granules were dried in the fluid bed dryer and passed through oscillating granulator.
4. The dried granules were compressed with the tabletting machine to form the core tablets.
5. The core tablets were coated with the film coated suspension (InstaCoat suspension) and formed the film coated tablets in a coating pan, e.g., Neocota (Automatic coating machine).

EXAMPLE-4

TABLE 4

A composition of the present invention including 100 mg of Imatinib.

| S. No. | Ingredients | mg/Tab |
|---|---|---|
| | Tablet core | |
| 1 | Imatinib Mesylate | 119.5 |
| 2 | Magnesium Stearate | 1.0 |
| 3 | Purified Water | q.s. |

TABLE 4-continued

A composition of the present invention including 100 mg of Imatinib.

| S. No. | Ingredients | mg/Tab |
|---|---|---|
| | Film coating | |
| 4 | InstaCoat | 2.5 |
| 5 | Purified water | q.s. |
| | Total weight of the tablet | 123 |

Procedure:

1. Magnesium Stearate was dispersed in the purified water to form the lubricant suspension.
2. Imatinib mesylate was granulated with the lubricant suspension obtained in step 1 in the rapid mixer granulator to form the wet granules.
3. The wet granules were dried in the fluid bed dryer and then passed through oscillating granulator.
4. The dried granules were compressed with the tabletting machine to form the core tablets.
5. The core tablets were coated with the film coated suspension (InstaCoat Suspension) and formed the film coated tablets in a coating pan, e.g., Neocota (Automatic coating machine).

EXAMPLE-5

TABLE 5

A composition of the present invention including 400 mg of Imatinib.

| S. No. | Ingredients | mg/Tab |
|---|---|---|
| | Intragranular portion | |
| 1 | Imatinib Mesylate | 478 |
| 2 | Purified Water | q.s. |
| | Extragranular portion | |
| 3 | Calcium Stearate | 3 |
| | Film coating | |
| 4 | InstaCoat | 9 |
| 5 | Purified water | q.s. |
| | Total weight of the tablet | 490 |

Procedure:

1. Imatinib mesylate was granulated with the purified water in the rapid mixer granules to form the wet granules.
2. The wet granules were dried in the fluid bed dryer and passed through oscillating granulator to form the dry granules.
3. The dry granules were lubricated with Calcium Stearate to form the lubricated blend.
4. The lubricated blend was compressed with the tabletting machine to form the core tablets.
5. The core tablets were coated with the film coating Suspension (InstaCoat Suspension) and formed the film coated tablets in a coating pan, e.g., Neocota (Automatic coating machine).

EXAMPLE-6

TABLE 6

A composition of the present invention including 100 mg of Imatinib.

| S. No. | Ingredients | mg/Tab |
|---|---|---|
| | Intragranular portion | |
| 1 | Imatinib Mesylate | 119.5 |
| 2 | Purified Water | q.s. |
| | Extragranular portion | |
| 3 | Calcium Stearate | 1.5 |
| | Film coating | |
| 4 | InstaCoat | 2 |
| 5 | Purified water | q.s. |
| | Total weight of the tablet | 123 |

Procedure:

1. Imatinib mesylate was granulated with the purified water in the rapid mixer granules to form the wet granules.
2. The wet granules were dried in the fluid bed dryer and passed through oscillating granulator.
3. The dry granules were lubricated with Calcium Stearate to form the lubricated blend.
4. The lubricated blend was compressed with the tabletting machine to form the core tablets.
5. The core tablets were coated with the film coating suspension (InstaCoat suspension) and formed the film coated tablets in a coating pan, e.g., Neocota (Automatic coating machine).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A tablet composition comprising an intragranular and an extragranular portion;
   at least 97% Imatinib mesylate by weight based on the total weight of the tablet composition; and
   a lubricant, wherein
   the lubricant is present in the extragranular portion of the tablet composition; and
   the lubricant is sodium stearyl fumarate.
2. A tablet composition of claim 1, wherein the lubricant is present in both the intragranular and extragranular portions of the tablet composition.
3. A tablet composition of claim 1, wherein the amount of lubricant is at least about 1% w/w of the total composition.
4. A process for the preparation of a tablet composition comprising at least 97% Imatinib mesylate by weight based on the total weight of the tablet composition, wherein the tablet composition comprises an intragranular and an extragranular portion, said process comprising wet granulation; wherein
- a lubricant is present in the extragranular portion of the tablet composition; and
- the lubricant is sodium stearyl fumarate.

5. A process according to claim 4 wherein the lubricant is present in both the extragranular and intragranular portions of the tablet composition.

* * * * *